United States Patent [19]

Spivack et al.

[11] 4,161,473
[45] Jul. 17, 1979

[54] 2,4,6-TRIALKYL-3-HYDROXYPHENYLALKANE PHOSPHONATE AND PHOSPHINATE STABILIZERS

[75] Inventors: John D. Spivack, Spring Valley; Martin Dexter, Briarcliff Manor, both of N.Y.

[73] Assignee: Ciba-Geigy Corporation, Ardsley, N.Y.

[21] Appl. No.: 668,358

[22] Filed: Mar. 19, 1976

Related U.S. Application Data

[60] Division of Ser. No. 491,074, Jul. 22, 1974, Pat. No. 3,962,376, which is a continuation-in-part of Ser. No. 400,602, Sep. 25, 1973, abandoned.

[51] Int. Cl.² ............................................. C08L 5/53
[52] U.S. Cl. ........................... 260/45.85 S; 252/46.6; 260/45.95 D; 260/45.8 NT; 260/45.95 F; 426/541
[58] Field of Search ............... 260/45.95 D, 45.85 S, 260/45.8 NT, 45.95 F, 398.5; 426/547; 252/46.6

[56] References Cited

U.S. PATENT DOCUMENTS 3,951,912  4/1976  Susi ................................. 260/45.85

*Primary Examiner*—V. P. Hoke
*Attorney, Agent, or Firm*—Luther A. R. Hall

[57] ABSTRACT

The compounds are trialkylsubstituted hydroxyphenylalkanephosphinates and phosphonates having the formula

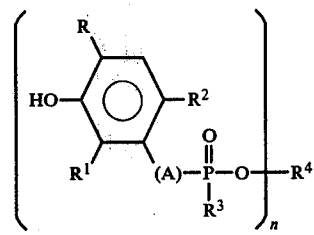

wherein R, $R^1$ and $R^2$ are independently lower alkyl or cycloalkyl groups, $R^3$ is alkyl, alkyl substituted with one halogen atom, phenyl, phenyl substituted with alkyl groups, alkoxy, alkoxy substituted with one halogen groups, phenoxy, phenoxy substituted with alkyl groups, alkylthioethoxy, alkyloxalkylenoxy, $R^4$ is alkyl, alkyl substituted with one halogen atom, cycloalkyl, phenyl, phenyl substituted with alkyl groups, alkylthioethyl, thiobisalkylene, alkylene, polyvalent cyclic or acyclic hydrocarbon radical, A is lower alkylene and n is 1 to 4.

These compounds are usually prepared by reacting the trialkylsubstituted hydroxybenzyl or hydroxyphenylalkyl halide with the appropriate tralkyl or triaryl phosphite or appropriate substituted phosphinite.

The compounds are useful as stabilizers of organic materials subject to oxidative, thermal and UV light deterioration.

15 Claims, No Drawings

2,4,6-TRIALKYL-3-HYDROXYPHENYLALKANE PHOSPHONATE AND PHOSPHINATE STABILIZERS

This is a divisional of application Ser. No. 491,074, filed July 22, 1974, now U.S. Pat. No. 3,962,376, issued June 8, 1976, which in turn is a continuation-in-part of the application Ser. No. 400,602, filed Sept. 25, 1973, now abandoned.

DETAILED DISCLOSURE

This invention pertains to trialkylsubstituted hydroxyphenylalkanephosphonates and phosphinates and to organic materials normally subject to oxidative, thermal and UV light deterioration stabilized with said phosphonates and phosphinates. More specifically, the compounds of this invention are those having the formula

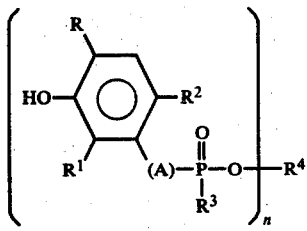

wherein $R, R^1$ and $R^2$ are independently lower alkyl of 1 to 8 carbons or cycloalkyl of 5 or 6 carbons, provided that there are at most 2 cycloalkyl groups present, $R^3$ is alkyl of 1 to 24 carbon atoms, alkyl of 1 to 24 carbon atoms substituted by one halogen atom, phenyl, phenyl substituted with alkyl groups, said alkyl groups having 1 to 18 carbon atoms, alkoxy of 1 to 24 carbon atoms, alkoxy of 1 to 24 carbon atoms substituted by one halogen atom, phenoxy, phenoxy substituted with alkyl groups, said alkyl groups having 1 to 18 carbon atoms, alkylthioethoxy of 5 to 27 atoms in the chain or alkylpolyoxyalkylenoxy of 5 to 28 atoms in the chain, $R^4$ is alkyl of 1 to 24 carbon atoms, alkyl of 1 to 24 carbon atoms substituted by one halogen atom, cycloalkyl of 5 to 6 carbon atoms, phenyl, phenyl substituted with alkyl groups, said alkyl groups having 1 to 18 carbon atoms, alkylthioethyl of 4 to 27 atoms in the chain, thiobisalkylene of 5 to 9 carbon atoms in the chain, alkyleneoxyalkylene of 5 to 9 atoms in the chain, polyoxyalkylene of 8 to 101 atoms, alkylpolyoxyalkylene of 4 to 27 atoms in the chain, alkylene of 2 to 12 carbon atoms or a polyvalent acyclic or cyclic hydrocarbon radical of 3 to 10 carbon atoms, A is straight or branched lower alkylene chain of 1 to 8 carbon atoms, and n is an integer of 1 to 4.

$R, R^1$ and $R^2$ groups can be straight or branched lower alkyl groups having 1 to 8 carbon atoms as, for example, methyl, ethyl, propyl, butyl, pentyl, heptyl or octyl. $R, R^1$ and $R^2$ groups can be cycloalkyl of 5 to 6 carbon atoms such as cyclopentyl or cyclohexyl. Preferably R is a branched alkyl group of 3 to 8 carbon atoms such as isopropyl, sec-butyl, tert-butyl, sec- and tert-pentyl, sec- and tert-hexyl, sec- and tert-heptyl or sec- and tert-octyl, and most preferably a tert-butyl group. $R^1$ and $R^2$ are preferably an alkyl group having 1 to 3 carbon atoms such as methyl, ethyl or n-propyl and most preferably the methyl group.

$R^3$ and $R^4$ can be alkyl of 1 to 24 carbon atoms such as methyl, n-butyl, n-octyl, n-dodecyl, n-octadecyl or n-tetracosanyl. Preferably $R^3$ and $R^4$ are alkyl groups of 1 to 18 carbon atoms such as n-dodecyl or n-octadecyl.

$R^3$ and $R^4$ are also phenyl or phenyl substituted with alkyl groups, said alkyl groups having 1 to 18 carbon atoms. The substituents may be methyl, isopropyl, tert-butyl and tert-octyl. Substitution in the ortho or para positions of the phenyl ring is especially preferred. Preferably $R^3$ and $R^4$ are phenyl substituted with alkyl groups having 1 to 12 carbon atoms and most preferably 1 to 8 carbon atoms such as methyl or two tert-butyl groups.

$R^3$ and $R^4$ are also an alkyl group of 1 to 24 carbon atoms substituted with one halogen group, preferably chlorine or bromine. Preferably $R^3$ and $R^4$ are 2-chloroethyl or 2-bromoethyl.

$R^3$ is also alkoxy of 1 to 24 carbon atoms substituted by one halogen group, preferably chlorine or bromine. Preferably $R^3$ is 2-chloroethoxy or 2-bromoethoxy.

The $R^3$ group can also be alkoxy of 1 to 24 carbon atoms such as methoxy, ethoxy, n-dodecyloxy, n-tetracosanyloxy. Preferably $R^3$ is alkoxy of 1 to 18 carbon atoms such as n-octadecyloxy.

$R^3$ is also phenoxy or phenoxy substituted with alkyl groups, said alkyl groups having 1 to 18 carbon atoms, preferably 1 to 8 carbon atoms, such as methyl, tert-butyl or tert-octyl.

$R^3$ is also alkylthioethoxy of 5 to 28 atoms in the chain such as 2-(n-tetracosanylthio)ethoxy, 2-(methylthio)ethoxy, 2-(n-butylthio)ethoxy, 2-(n-octadecylthio)ethoxy or 2-(n-dodecylthio)ethoxy. Preferably $R^3$ is alkylthioethoxy of 6 to 22 atoms in the chain.

$R^3$ is alkylpolyoxyalkylenoxy of 5 to 28 atoms in the chain and having the general structure $R°(OCH_2CH_2)_hO-$ where $R°$ is alkyl of 1 to 18 carbon atoms and h is 1 to 3. Preferably $R^3$ is alkylpolyoxyalkylenoxy of 6 to 22 carbon atoms.

$R^4$ can be cycloalkyl of 5 to 6 carbon atoms such as cyclopentyl and cyclohexyl.

$R^4$ is also alkylthioethyl of 4 to 27 atoms in the chain such as 2-methylthioethyl, 2-(n-octylthio)ethyl and 2-(n-tetracosanylthio)ethyl. Preferably $R^4$ is alkylthioethyl of 5 to 21 atoms in the chain.

Where n is 2, $R^4$ is also thiobis-alkylene of 5 to 9 atoms in the chain. Preferably $R^4$ is thiodiethylene.

$R^4$ is also alkylene of 2 to 12 carbon atoms such as ethylene, tetramethylene, 2,2-dimethylpropylene and dodecamethylene. Preferably $R^4$ is alkylene of 2 to 8 carbon atoms and most preferably of 2 to 6 carbon atoms.

$R^4$ can be alkyleneoxyalkylene of 5 to 9 atoms in the chain such as oxydiethylene, oxydibutylene and oxydi(1,2-propylene). Preferably $R^4$ is oxydiethylene.

$R^4$ can also be polyoxyalkylene of 8 to 101 atoms having the general formula $—R°°(OR°°)_k—$ where $R°°$ is a straight or branched lower alkylene of 2 to 4 carbon atoms and k is 2 to 33. $R°°$ is ethylene, 1,2-propylene, 1,2-butylene and tetramethylene. Preferably $R^4$ is polyoxyalkylene of 8 to 11 atoms in the chain where $R°°$ is ethylene and k is 2 to 3. Most preferably $R^4$ is polyoxyethylene of 8 atoms in the chain.

$R^4$ can also be alkylpolyoxyalkylene of 4 to 27 atoms in the chain having the general structure $R°(OCH_2CH_2)_h—$ where $R°$ is alkyl of 1 to 18 carbon atoms and h is 1 to 3. Preferably $R^4$ is alkylpolyoxyethylene of 5 to 21 atoms in the chain.

Where n is 3 to 4, $R^4$ is a polyvalent acyclic or cyclic hydrocarbon radical of 3 to 10 carbon atoms such as 1,2,3-propanetriyl, neopentanetriyl, neopentanetetrayl, 2,2-di-methyl-1,2,3-pentanetriyl. Preferably $R^4$ is a polyvalent acyclic hydrocarbon radical of 3 to 7 carbon atoms.

A is a straight chain alkylene chain of 1 to 8 carbon atoms, preferably of 1 to 4 carbon atoms, and most preferably of 1 to 2 carbon atoms such as methylene and ethylene. Of particular importance are the compounds where A is methylene.

A can be a branched alkylene of 2 to 8 carbon atoms such as ethylidene, 1,1-n-butylidene and 1,1-n-octylidene.

n is an integer of 1 to 4, preferably of 1 to 2 and most preferably 1

Compounds of formula I where n=1, are made by the reaction of a compound of the formula II

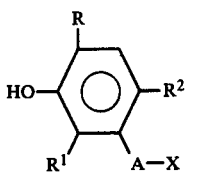

(II)

where X is halogen (e.g., chlorine or bromine) or hydroxyl, in turn prepared by conventional halogenomethylation or hydroxymethylation procedures on the corresponding trisubstituted phenol of formula VII with a tertiary phosphite of the formula III $P(OR^4)_3$ (III)

Substitution of higher aldehydes such as n-butyraldehyde and n-octanol for formaldehyde in these procedures lead to the preparation of compounds of formula II where A is 1,1-alkylidene.

Compounds of formula I where n=1, are also made by the reaction of a tertiary phosphonite of the formula IV $R^3—P(OR^4)_2$ (IV)

to yield respectively the products where $R^3$ is the same as $OR^4$ or where $R^3$ is an alkyl or aryl directly bonded to phosphorus as defined in formula I above. Other suitable synthetic routes, where n=1, include the reaction of the compound II with an alkali or metal salt of a dialkyl phosphite or diaryl phosphite of the formula V

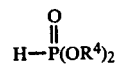

(V)

or a phosphinite of the formula VI

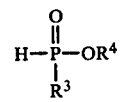

(VI)

in the case where the $R^3$ is an alkyl or aryl group directly bonded to phosphorus.

Compounds where n=2 to 4, and where $R^3$ is alkyl or aryl directly bonded to phosphorus, are made by transesterification of the appropriate aryl (e.g., phenyl) phosphinate with a polyol or polyhydric phenol.

2-(Alkylthio)ethyl phosphonates are conveniently made by reacting the corresponding 2-chloroethyl phosphonates with an alkyl mercaptan.

Phenols used in the syntheses of the compounds of formula II have the formula VII

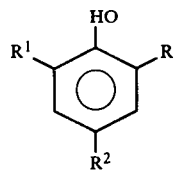

(VII)

where R, $R^1$ and $R^2$ are as previously defined. Of particular interest are those in which $R^1$ and $R^2$ are preferably methyl since these are readily prepared from commercially available 2,4-xylenol. Thus, for example, the preparation of 2,4-dimethyl-6-tert.-butylphenol is described by G. Parc in the Revue de l'Institut Francais Du Petrole, vol. XV, page 689 (1960).

The trialkylsubstituted hydroxyphenylalkanephosphonates and phosphinates of this invention are stabilizers of organic material normally subject to thermal and oxidative deterioration. Materials which are thus stabilized include synthetic organic polymeric substances such as vinyl resins formed from the polymerization of vinyl halides or from the copolymerization of vinyl halides with unsaturated polymerizable compounds, e.g., vinyl esters, α,β-unsaturated ketones, α,β-unsaturated aldehydes and unsaturated hydrocarbons such as butadienes and styrene; poly-α-olefins such as polyethylene, polypropylene, polybutylene including copolymers of α-olefins such as ethylene/propylene copolymer, dienes such as polybutadiene, polyisoprene, and the like, including copolymers with other monomers; polyurethanes and polyamides such as polyhexamethylene adipamide and poly-caprolactam; polyesters such as polyethylene terephthalates; polyphenylene oxide and copolymers; polycarbonates; polyesters such as polyethylene terephthalate; polyacetal; polystyrene, polyethylene oxide; and copolymers such as those of high impact polystyrene containing copolymers of butadiene and styrene and those formed by the copolymerization of acrylonitrile, butadiene and/or styrene; natural and synthetic rubbers such as ethylene/propylene/diene copolymer (EPDM) and chlorinated rubber.

Other materials which can be stabilized by the compounds of the present invention include lubricating oil of the -ethylhexyl) ester type, i.e., di(2-ethylhenyl) azelate and other synthetic ester lubricants pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethylene glycol, methoxytriethylene glycol, triethylene glycol, octaethylene glycol, dibutylene glycol, α-dipropylene glycol and the like.

The substrates of particular importance are polymers such as polyethylene and polypropylene. Polypropylene is especially well stabilized with the compounds of this invention.

In general, the stabilizers of this invention are employed from about 0.01 to about 5% by weight of the stabilized composition, although this will vary with the particular substrate and application. An advantageous range is from about 0.05 to about 2% and especially from 0.1 to about 1%.

For addition to polymeric substrates, the stabilizers can be blended before polymerization or after polymerization, during the usual processing operations, for example, by hot-milling, the composition then being extruded, pressed, or the like into films, fibers, filaments, hollow spheres and the like. The heat stabilizing properties of these compounds advantageously stabilize the polymer against degradation during such processing at the high temperature generally encountered. The stabilizers can also be dissolved in suitable solvents and sprayed on the surface of films, fabrics, filaments or the like to provide effective stabilization.

These compounds can also be used in combination with other additives such as sulfur-containing esters, e.g., distearyl β-thiodipropionate (DSTDP), dilauryl β-thiodipropionate (DLTDP) in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, di- and tri-alkyl- and alkylphenyl-phosphites, heat stabilizers, ultraviolet light stabilizers, antiozonants, dyes, pigments, fillers, surface active agents, metal chelating agents, dyesites and the like. Often combinations such as these, particularly the sulfur-containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

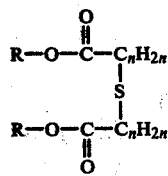

wherein R is an alkyl group having from 6 to 24 carbon atoms; and n is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

The stabilizers of this invention are particularly useful in polymer formulations because of their ability to stabilize polymers during high temperature processing. Furthermore, polymer formulations containing them are resistant to gas fading.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.1 to 1%. Illustrative examples of light stabilizers are listed below.

UV-absorbers and light protection agents 2-(2'-Hydroxyphenyl)-benztriazoles, such as, for example, the 5'-methyl-, 3',5'-di-tert.-butyl-,5'-tert.-butyl-, 5'-(1,1,3,3-tetramethyl-butyl)-, 5-chloro-3',5'-di-tert.-butyl-, 5-chloro-3'-tert.-butyl-5'-methyl-, 3'-sec.-butyl-5'-tert.-butyl, 3'-[α-methyl-benzyl]-5'-methyl-, 3'-[α-methylbenzyl]-5'-methyl-5-chloro-, 4'-hydroxy-, 4'-methoxy-, 4'-octoxy-, 3',5'-di-tert.-amyl-, 3'-methyl-5'-carbomethoxyethyl- or 5-chloro-3',5'-di-tert.-amyl-derivatives.

2,4-Bis-(2'-hydroxyphenyl)-6-alkyl-s-triazines, such as, for example, the 6-ethyl-, 6-undecyl- or 6-heptadecyl-derivatives.

2-Hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivatives.

1,3-Bis-(2'-hydroxy-benzoyl)-benzenes, such as, for example, 1,3-bis(2'-hydroxy-4'-hexyloxy-benzoyl)-benzene, 1,3-bis-(2'-hydroxy-4'-octoxy-benzoyl)-benzene and 1,3-bis(2'-hydroxy-4'-dodecyloxy-benzoyl)-benzene.

Esters of optionally substituted benzoic acids, such as for example, phenyl salicylate, octylphenyl salicylate, dibenzoylresorcinol, bis-(4-tert.-butylbenzoyl)-resorcinol, benzoyl-resorcinol, 3,5-di-tert.-butyl-4-hydroxybenzoic acid 2,4-di-tert.-butyl-phenyl ester, octadecyl ester or 2-methyl-4,6-di-tert.-butylphenyl ester.

Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methyl-indoline.

Nickel compounds, such as, for example, nickel complexes of 2,2'-thio-bis[4-(1,1,3,3-tetramethyl butyl)-phenol] such as the 1:1 and 1:2 complex, optionally with other ligands such as n-butylamine, triethanolamine or N-cyclohexyl-diethanolamine; nickel complexes of bis-[2-hydroxy-4-(1,1,3,3-tetramethyl butyl)-phenyl]-sulphone, such as the 2:1 complex, optionally with other ligands such as 2-ethyl-caproic acid; nickel dibutyldithiocarbamate, nickel salts of 4-hydroxy-3,5-di-tert.-butyl-benzylphosphonic acid monoalkyl esters, such as the methyl, ethyl or butyl ester, the nickel complex of (2-hydroxy-4-methyl-phenyl)-undecyl-ketonoxime and nickel 3,5-di-tert.-butyl-4-hydroxy-benzoate.

Oxalic acid diamides, such as, for example, 4,4'-dioctyloxyoxanilide, 2,2'-dioctyloxy-5,5'-di-tert.-butyl-oxanilide, 2,2'di-dodecyloxy-5,5'-di-tert.-butyl oxanilide, 2-ethoxy-5-tertiarybutyl-2'-ethyloxanilide, 2-ethoxy-2'-ethyl-oxanilide, N,N'-bis-(3-dimethylaminopropyl) oxalamide, mixtures of o- and p-methoxy and o- and p-ethoxy di-substituted oxanilides and mixtures of 2-ethoxy-5-tert.-butyl-2'-ethyl-oxanilide with 2-ethoxy-2'-ethyl-5,4'-di-tert.-butyl-oxanilide.

Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl)sebacate and 3-n-octyl-7,7,9,9,-tetramethyl-1,3-triaza-spiro [4,5] decane-2,4-dione.

For exemplification purposes only, listed below are compounds of this invention which are useful as stabilizers as discussed above:

dimethyl 4-tert.-butyl-2,6-dimethyl-3-hydroxybenzyl phosphonate bis-(2-chloroethyl) 4-tert.-butyl-2,6-dimethyl-3-hydroxybenzylphosphonate di-(2-ethylhexyl) 4-tert.-butyl-2,6-dimethyl-3-hydroxybenzylphosphonate di-n-tetracosyl 4-tert.-butyl-2,6-dimethyl-3-hydroxybenzylphosphonate bis[2-(n-octadecylthio)ethyl] 4-tert.-butyl-2,6-dimethyl-3-hydroxybenzylphosphonate dimethyl 4-tert.-octyl-2,6-dimethyl-3-hydroxybenzylphosphonate di-n-octadecyl 2,4,6-trimethyl-3-hydroxybenzylphosphonate di-n-octyl 4-tert.-butyl-2,6-dimethyl-3-hydroxybenzylphosphonate bis [2-(n-dodecylthio)ethyl] 1-(4-tert.-butyl-2,6-dimethyl 3-hydroxybenzyl)ethanephosphonate 2,2-dimethylpropylene bis[(2,4 diisopropyl-3-hydroxy-6-methylphenethyl)methanephosphinate]

neopentanetrixl tris-[(4-tert.-butyl-2,6-dimethyl-3-hydroxybenzyl)]benzenephosphinate neopentanetetrayl tetrakis-[(4-tert.-butyl-2,6-dimethyl-3-hydroxybenzyl)ethanephosphinate]

di-(p-tert.-octylphenyl) 4-tert.-butyl-2,6-dimethyl-3-hydroxybenzylphosphonate diphenyl 4-tert.-butyl-2,6-dimethyl-3-hydroxybenzylphosphonate di-o-tolyl 4-tert.-butyl-2,6-dimethyl-3-hydroxybenzylphosphonate di-(2,4-di-tert.-butylphenyl) 4-tert.-butyl-2,6-dimethyl-3-hydroxybenzylphosphonate n-octadecyl (2,6-dimethyl-3-hydroxy-4-tert. octylbenzyl)benzenephosphinate The following examples are illustrative of the invention but are not meant to limit the scope of same. In said examples, parts are by weight unless otherwise indicated and the relationship between parts by weight and parts by volume is as that between grams and cubic centimeters. The temperatures are in degrees centigrade.

EXAMPLE 1

6-tert.-Butyl-3-chloromethyl-2,4-dimethylphenol

The compound of this example was made by a procedure described by Wegler and Regel (Makr. Chem. 9, 22 (1952)). After crystallization from petroleum ether, the product of the Example is obtained as white crystals melting at 45° to 47°.

EXAMPLE 2

Dimethyl 4-tert.-Butyl-2,6-dimethyl-3-hydroxybenzylphosphonate

To 16.1 grams 6-tert.-butyl-3-chloromethyl-2,4-dimethylphenol dissolved in 40 ml. of dry n-heptane was added 9.55 grams of trimethyl phosphite. One-third of the trimethyl phosphite was initially added dropwise at room temperature, the remainder being added dropwise at 70°. The reaction mixture was then heated at reflux (97°) for ten hours and the residual white solid isolated by stripping off the volatiles by distillation at 50° to 60° at reduced pressure. The residue was triturated twice with petroleum ether and recrystallized, after clarification, from a solvent mixture of n-hexane and isopropanol yielding the desired product as white crystals melting at 146° to 148°. (compound 1)

EXAMPLE 3

6-tert.-Octyl-3-chloromethyl-2,4-dimethylphenol

The compound of this example was made by a procedure analogous to the compound of Example 1. After crystallization from petroleum ether the desired compound is isolated as white crystals melting at 80° to 83°.

EXAMPLE 4

Bis-(2-chloroethyl) 4-tert.-butyl-2,6-dimethyl-3-hydroxybenzylphosphonate

The title compound was made by a similar procedure to that described in Example 2 by substituting tris-(2-chloroethyl) phosphite for trimethyl phosphite. The desired compound was obtained as white crystals melting at 127° to 130° after trituration with an 80:20 solvent mixture of hexane and benzene. (compound 2)

EXAMPLE 5

Di-n-dodecyl 4-tert.-butyl-2,6-dimethyl-3-hydroxybenzylphosphonate

41 Grams of trilauryl phosphite and 16.1 grams of 6-tert.-butyl-3-chloromethyl-2,4-dimethylphenol were stirred together as a melt at 105° to 110° for 1 hour, followed by 110° to 120° for 2 hours, 120° to 125° for 10 hours and finally at 140° to 145° for 4 hours. The crude was topped in the "ASCO 50" Rotafilm Molecular Still at a wall temperature of 80° to 90° at 1 to 5 microns Hg. pressure to remove most of the by-product dodecyl chloride as well as small amounts of other volatiles. This topping procedure was repeated at a wall temperature of 200° to 210° at the same pressure to remove additional volatiles. The desired product distilled at a wall temperature of 250° to 260° at 1 micron Hg. pressure yielding the desired product as a colorless liquid which solidified to a white solid (m.p. 36° to 42°). (compound 3)

EXAMPLE 6

Di-n-octadecyl 4-tert.-butyl-2,6-dimethyl-3-hydroxybenzylphosphonate 21.7 Grams of trioctadecyl phosphite and 5.75 grams 6-tert.-butyl-3-chloromethyl-2,4-dimethylphenol was stirred together as a melt at 110° to 120° for 2 hours and at 120° to 125° for 7 hours. The reaction mixture was dissolved in 100 ml. of toluene and the colorless, slightly turbid solution was successively washed with 3 N aqueous hydrochloric acid, water, 2 N aqueous sodium carbonate solution and water until the wash waters were neutral. After drying over anhydrous sodium sulfate and filtering free of drying agent, the clear filtrate was concentrated by distillation of the solvent at reduced pressures. The residual oil was topped in the "ASCO 50" Rota-Film Molecular Still at a wall temperature of 210° to 215° and a pressure of 1 to 5 microns. After crystallization from methylethyl ketone, the desired product was obtained as white crystals melting at 70° to 72.5°. (compound 4)

EXAMPLE 7

Bis[2-(n-octadecylthio)ethyl] 4-tert.-butyl-2,6-dimethyl-3-hydroxybenzylphosphonate 9.0 Grams of n-octadecyl mercaptan dissolved in 30 ml. of xylene was added rapidly to 0.72 grams of sodium sand dispersed by rapid stirring in 150 ml. of xylene at 60°. The reaction mixture was stirred at 80° to 105° for 25 minutes and then kept at 100° to 105° for 15 minutes yielding a white dispersion of sodium n-octadecyl mercaptide. 2.0 Ml. of dry N,N-dimethylformamide was added to the reaction mixture. 5.96 Grams of bis-(2-chloroethyl) 4-tert.-butyl-2,6-dimethyl-3-hydroxybenzylphosphonate (Example 4) dissolved in 70 ml. of hot xylene was added dropwise to the reaction mixture. The reaction mixture was then heated at 120° for 10 hours. The clear yellow xylene solution was successively washed with 3 N aqueous hydrochloric acid, water, and aqueous saturated sodium chloride until the wash liquors were neutral. After drying overnight over anhydrous sodium sulfate and magnesium sulfate and removing the drying agents by filtration, the clear filtrate was freed of solvent by distillation at reduced pressures. The residue was first crystallized from a solvent mixture of isopropanol-methanol, the hot solution being freed of an insoluble oil by decantation, the supernatant liquid depositing crystals on cooling in an ice-water mixture. The crystals were then recrystallized again from isopropanol-methanol by first dissolving them in isopropanol, filtering off an insoluble solid after cooling to room temperature, then adding a little methanol and cooling overnight at 15°. In this manner, the desired compound was obtained as white crystals melting at 57° to 63°. (compound 5)

EXAMPLE 8 n-Octadecyl (2,6-dimethyl-3-hydroxy-4-tert.-octylbenzyl) benzenephosphinate 5.8 Grams of 6-tert.-octyl-3-chloromethyl-2,4-dimethylphenol and 13.4 grams of di-n-octadecyl phenylphosphonite are heated together at about 135° at 15 mm, Hg. nitrogen pressure for about 2 hours. The reaction product is then heated at 190° to about 220° at 0.2 to 0.8 mm Hg. to remove the n-octadecyl chloride formed as by-product, and to recover the product.

Unstabilized polypropylene powder (Hercules Profax 6501) was thoroughly blended with 0.2% by weight of the indicated stabilizer compound. Also prepared were samples of polypropylene containing 0.1% by weight of the same stabilizer and 0.3% by weight of distearyl β-thiodipropionate (DSTDP). The blended materials were then milled on a two-roll mill at 182° C. for 10 minutes, after which time the stabilized polypropylene was sheeted from the mill and allowed to cool.

The milled polypropylene sheets were then cut into pieces and pressed for 7 minutes on a hydraulic press at 218° C., 19.25 Kg/cm² pressure. The resulting plaques of 0.635 mm thickness were tested for resistance to accelerated aging in a forced draft over at 150° C.

When the plaques showed the first signs of decomposition (e.g., cracking or brown edges), they were considered to have failed. The results are shown in Table I below.

TABLE I

OVEN AGING OF POLYPROPYLENE
Containing Stabilizers of the Invention

| Ex. No. | Percent Stabilizer | Hours to Failure |
|---|---|---|
| 9 | No stabilizer | 3 |
| 10 | 0.2% Compound 1 | <20 |
| 11 | 0.1% Compound 1 + 0.3% DSTDP | 70 |
| 12 | 0.2% Compound 2 | <20 |
| 13 | 0.1% Compound 2 + 0.3% DSTDP | 75 |
| 14 | 0.2% Compound 3 | 235 |
| 15 | 0.1% Compound 3 + 0.3% DSTDP | 1085 |
| 16 | 0.2% Compound 4 | 235 |
| 17 | 0.1% Compound 4 + 0.3% DSTDP | 1510 |
| 18 | 0.2% Compound 5 | 95 |
| 19 | 0.1% Compound 5 + 0.3% DSTDP | 310 |

EXAMPLE 20

Pellets (500 g) of unstabilized nylon-6,6 (Zytel 101, DuPont) are placed in a Kitchen Aid Mixer. With mixing a solution of 0.5% (based on the weight of nylon) of di-n-dodecyl 4-tert.-butyl-2,6-dimethyl-3-hydroxybenzylphosphonate in 20 ml of methylene chloride is added slowly. Sodium hypophosphite (0.5 gm. 0.1%) is dissolved in 20 ml of water and added slowly with mixing to the nylon pellets after the antioxidant solution has been added and most of the methylene chloride has evaporated. The stabilized pellets are dried at 80° C. at <<1 mm Hg. for 4 hours.

The polyamide formulation is extruded at 315.6° C. through at 0.635 cm die into a rod which is water cooled and chopped into pellets. A 1.905 cm Brabender extruder, equipped with a nylon screw, is used. The pellets are dried at 80° C. at <1 mm for 4 hours.

The dried pellets are compression molded into 0.127 mm thick film by pressing at 290° C. for 4 minutes at 57.75 Kg/cm². The films are oven aged at 150° C. in a forced draft oven and samples are removed periodically. The specific viscosity of the samples are determined using a 1% formic acid solution at 25° C. The sample stabilized with the above noted stabilizer required longer aging time to reduce its viscosity by one-half than the unstabilized sample.

EXAMPLE 21

Unstabilized high impact polystyrene resin is dry blended with 0.01% by weight of the resin of n-octadecyl (2,6-dimethyl-3-hydroxy-4-tert.-octylbenzyl)benzenephosphinate. The resin is then extrusion compounded on a 2.54 cm 24/1=L/D extruder, melt temperature 260° C. and pressed for 7 minutes at a temperature of 163° C. and a pressure of 140 Kg/cm² into a sheet of uniform thickness of 0.752 mm. The sheets are then cut into plaques of 5.08 cm×5.08 cm. The plaques are then oven aged at 80° and color measurements made periodically using a Hunter Color Difference Meter Model D25. The polystyrene samples stabilized with the above stabilized develops the undesirable yellow discoloration substantially later than the time that such discoloration occurred in the unstabilized samples.

EXAMPLE 22

Unstabilized linear polyethylene (HiFax 4401) is solvent blended in methylene chloride with 0.5% by weight of the substrate of di-n-octyl 4-tert.-butyl-2,6-dimethyl-3-hydroxybenzylphosphonate and then vacuum dried. The resin is then extruded at 232.2° C. using a 1.905 cm extruder having a 24:1 L/D ratio. The melt flow rate of a sample of the resin is determined after each extrusion according to ASTM test D-1238. Polyethylene stabilized with above compound is found to undergo less change in the melt flow rate than the unstabilized polyethylene.

EXAMPLE 23

A quantity of SBR emulsion containing 100 g of rubber (500 ml of a 20% emulsion obtained from Texas US as Synpol 1500) previously stored under nitrogen, is placed in a beaker and stirred vigorously. The pH of the emulsion is adjusted to 10.5 with a 0.5 N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40°–45° C.

The dried rubber (25 g) is heated under nitrogen at 125° C. in a Brabender mixer and to this is added with mixing 0.1% bis[2-(n-octadecylthio)ethyl]4-tert.-butyl 2,6-dimethyl-3-hydroxybenzylphosphonate. The composition is mixed for 5 minutes after which it is cooled and compression molded at 125° C. into 12.7 cm×0.635 mm plaques. The plaques are oven aged at 100° C. At various intervals gel content is determined on the rubber. The rubber stabilized with the above compound shows much less gel formation than the unstabilized sample.

EXAMPLE 24

To 50 g of polyacetal resin containing 0.1% of an acid scavenger, dicyandiamide, is added 0.2% by weight of dimethyl 4-tert.-butyl-2,6-dimethyl-3-hydroxybenzylphosphonate and milled for 7 minutes at 200° C. in a Brabender Plasti-recorder. The milled formulation is subsequently pressed into a 1.016 mm sheet at 215° C. at 24.5 Kg/cm² for 90 seconds then cooled quickly in a cold press at 24.5 Kg/cm². The stabilized sheets are then remolded for 2 minutes at contact pressure and for 3 minutes at 21 Kg/cm² at 215° C. to give plaques 3.81 cm×5.715 cm×3.175 mm. The plaques are aged in the oven at 60° C. and the weight loss of the specimen is determined periodically until a 4% weight loss is reached. The stabilized sample takes a much longer time to reach this 4% weight loss than does the unstabilized sample.

EXAMPLE 25

Unstabilized thoroughly dried polyethylene terephthalate chips are dry blended with 1.0% of di-n-octadecyl 4-tert.-butyl-2,6-dimethyl-3-hydroxybenzylphosphonate 60/10 denier multifilament is melt spun at a melt temperature of 290° C. and cold oriented 3 to 1. The oriented fibers are wound into skeins and oven aged at 140° C. The stabilized material exhibits greater retention of tensile strength after 24 hours than the unstabilized material.

EXAMPLE 26

A stabilized high temperature lubricating oil is prepared by incorporating 0.05% by weight of diphenyl 4-tert.-butyl-2,6-dimethyl-3-hydroxybenzylphosphonate to the lubricant which comprises diisoamyl adipate. The stabilized composition is compared with the unstabilized lubricant by heating at 175° C. in the presence of air and metallic cataysts according to the test method described in Military Specification Mil-I-7808c. After 72 hours, the blank containing no stabilizer contains more sludge and has a greater viscosity than the stabilized lubricant.

What is claimed is:

1. A composition of matter comprising an organic material normally subject to deterioration and from 0.01 to 5% by weight of a stabilizing compound of the formula

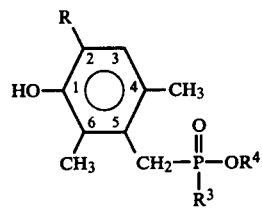

wherein R is alkyl of 4 to 8 carbon atoms, $R^3$ is alkoxy of 12 to 24 carbon atoms, and $R^4$ is alkyl of 12 to 24 carbon atoms.

2. A composition according to claim 1 wherein the stabilizing compound is di-n-dodecyl 4-tert-butyl-2,6-dimethyl-3-hydroxybenzylphosphonate.

3. A composition according to claim 1 wherein the stabilizing compound is di-n-octadecyl 4-tert-butyl-2,6-dimethyl-3-hydroxybenzylphosphonate.

4. A composition of claim 1 containing additionally from 0 to 2% by weight of a thio co-stabilizer having the formula

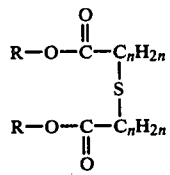

wherein R is alkyl of 6 to 24 carbons and n is an integer of 1 to 6.

5. A composition of claim 1 containing additionally from 0 to 5% by weight of a light stabilizer.

6. A composition of claim 4 wherein the organic material is polyolefin.

7. A composition of claim 4 containing additionally from 0 to 5% by weight of a light stabilizer.

8. A composition comprising a polyolefin containing a stabilizing quantity of (a) a compound of the formula:

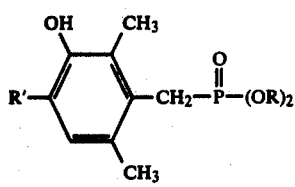

wherein R is an alkyl group of 12 to 24 carbon atoms and R' is a branched-chain alkyl of 3 to 8 carbon atoms and (b) a secondary stabilizer selected from the group consisting of distearyl thiodipropionate and dilauryl thiodipropionate.

9. A composition as defined in claim 8 wherein said stabilizing quantity is 0.01 to 2.0 percent on weight of polyolefin of said compound and 0.1 to 1.0 percent on weight of polyolefin of said secondary stabilizer.

10. A composition as defined in claim 8 wherein said polyolefin is polypropylene.

11. A composition as defined in claim 8 wherein R is dodecyl.

12. A composition as defined in claim 8 wherein R is octadecyl.

13. A composition as defined in claim 8 wherein R' is tert-butyl.

14. A composition as defined in claim 13 wherein R is dodecyl.

15. A composition as defined in claim 13 wherein R is octadecyl.

* * * * *